United States Patent
Rolfes et al.

(10) Patent No.: US 11,191,715 B2
(45) Date of Patent: Dec. 7, 2021

(54) HAIR CONDITIONER COMPOSITION UTILIZING A HEAT STYLING RESPONSIVE FILM

(71) Applicant: Kao USA Inc., Cincinnati, OH (US)

(72) Inventors: Michelle Rolfes, Amelia, OH (US); Adam Schrott, Hebron, KY (US)

(73) Assignee: Kao USA Inc., Cincinnati, OH (US)

( * ) Notice: Subject to any disclaimer, the term of this patent is extended or adjusted under 35 U.S.C. 154(b) by 719 days.

(21) Appl. No.: 15/878,890

(22) Filed: Jan. 24, 2018

(65) Prior Publication Data

US 2019/0224108 A1   Jul. 25, 2019

(51) Int. Cl.
| | | |
|---|---|---|
| A61Q 5/06 | (2006.01) |
| A61K 8/92 | (2006.01) |
| A61K 8/41 | (2006.01) |
| A61K 8/34 | (2006.01) |
| A61K 8/31 | (2006.01) |
| A61K 8/42 | (2006.01) |
| A61Q 5/12 | (2006.01) |
| A61K 8/46 | (2006.01) |

(52) U.S. Cl.
CPC .............. *A61K 8/922* (2013.01); *A61K 8/31* (2013.01); *A61K 8/342* (2013.01); *A61K 8/416* (2013.01); *A61K 8/42* (2013.01); *A61K 8/463* (2013.01); *A61Q 5/06* (2013.01); *A61Q 5/12* (2013.01); *A61K 2800/24* (2013.01)

(58) Field of Classification Search
None
See application file for complete search history.

(56) References Cited

U.S. PATENT DOCUMENTS

| | | | | |
|---|---|---|---|---|
| 7,906,107 B2 * | 3/2011 | Maillefer | ............... | A61K 8/375 424/47 |
| 2013/0142748 A1 * | 6/2013 | Tamura | ..................... | A61Q 5/02 424/70.12 |
| 2015/0007849 A1 * | 1/2015 | Cajan | ....................... | A45D 7/04 132/203 |
| 2016/0331657 A1 * | 11/2016 | Lyons | .................... | A61K 8/416 |

* cited by examiner

*Primary Examiner* — Jyothsna A Venkat

(74) *Attorney, Agent, or Firm* — Frost Brown Todd LLC

(57) ABSTRACT

A hair care composition having a combination of a high melting point wax to provide a hydrophobic film (frizz resistance) and thermo-pliable film (heat styling response), along with a lightweight conditioner, to produce a hair care composition that is far less susceptible to buildup than traditional products currently marketed.

3 Claims, No Drawings

HAIR CONDITIONER COMPOSITION UTILIZING A HEAT STYLING RESPONSIVE FILM

FIELD OF THE INVENTION

The present invention provides the qualities expected from a hair conditioner coupled with a unique thermo-pliable film that responds to heat from common consumer hair styling appliances.

BACKGROUND

Consumers desire sufficient detangling, moisturization, and frizz control from hair conditioners that aid in achieving their desired style.

In washing, drying, and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel. Generally, these benefits are provided by a separate hair conditioning product.

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. This approach presents several significant drawbacks to the user. It requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition.

Many modern hair styles require the use of heat tools to dry and style hair to reach a desired look. However, often consumers are frustrated by the use of such tools as they produce unmanageable hair and increase the occurrence of undesirable features such as frizz and flyaways.

It has now been discovered that two separate hair care benefits, i.e., conditioning and styling, can be provided by a single hair care product. In addition, the present invention provides for the ability to use low temperature heat of common consumer hair appliances to produce immediate manageability of hair, wherein the average maximum temperature is less than 110° C.

BRIEF SUMMARY

Existing rinse-off products attempt to provide improved styling with consumer hair appliances through the application of high concentration of quaternary ammonium cationic surfactant compounds that can build up on hair, leaving it feeling greasy and weighed down. Subsequent uses of the conditioner increase static-induced frizz due to the bulky nature of the compounds and increased static repulsion between fibers as a result. High viscosity dimethicone/dimethiconols/amodimethicones can also feel greasy and leave hair feeling weighed down.

Existing leave-on products attempt to provide protection from heat and frizz through the application of high volatility silicones (phenyltrimethicone/caprylyl trimethicone/cyclohexasiloxane/cyclopentasiloxane) that may provide only temporary shine during styling. High viscosity dimethicone/dimethiconols/amodimethicones that are used for heat protection may also leave the hair greasy and weighed down.

This technology relates to a hair care composition comprising a high melting point waxy material to provide a hydrophobic and thermo-pliable film along with a lightweight conditioner, to produce a hair care composition that is far less susceptible to buildup than products currently marketed. The inclusion of a neutralizing acid, e.g. glyoxylic acid, acts to control the deposition of the thermos-pliable film to minimize unacceptable buildup on hair.

DETAILED DESCRIPTION

The present invention provides the qualities expected from a conditioner coupled with a unique thermo-pliable film that responds to heat generated by common consumer hair styling appliances. The composition may be applied to wet hair as a rinse off product and/or applied to damp or dry hair as a leave-on product.

This thermo-pliable hair care and styling composition comprises an alkyl amine cationic surfactant having a molecular weight from about 400 g/mol to about 500 g/mol. The amount of alkyl amine cationic surfactant present in the composition may range from about 0.1% to about 7% by weight of, or from about 0.1 to about 5% by weight, or from about 1% to about 3% by weight, or from about 2% to about 5% by weight. The alkyl amine cationic surfactant may be selected from behentrimonium chloride, behenamidopropyl dimethylamine, behentrimonium methosulfate, and mixtures thereof.

The composition may also contain from about 0.1% to 15% long chain fatty alcohols. Examples of such alcohols include behenyl alcohol, cetyl alcohol, stearyl alcohol, cetearyl alcohol, arachidyl alcohol, and mixtures thereof. The melting point of long chain fatty alcohol is from about 45° C. to about 80° C.

The composition may also contain a high melting point waxy material, having a melting point from about 65° C. to about 90° C., present in amounts ranging from about 0.1% to about 5% (by weight); 1% to about 3% (by weight); or from about 0.75% to about 1.5% (by weight). Specifically, the high melting point waxy material may be selected from natural waxes, hydrocarbon waxes, and mixtures thereof, for instance, and not limited to, paraffin wax, ozokerite wax, ceresine wax, carnauba wax, rice bran wax, and mixtures thereof. Also, the composition may also contain from about 0.1 to 3% of neutralizing $C_2$ to $C_4$ carboxylic acid with an individual $pK_a$ from about 3.1 to about 4.6. Such neutralizing carboxylic acids may be selected from oxalic acid, glycolic acid, lactic acid, succinic acid, malic acid, and mixtures thereof. A suitable hair care carrier may also be utilized, wherein the point at which the composition first begins to melt is less than or equal to any solid materials utilized in the composition. The ratio of the cationic surfactant to the long chain fatty alcohol is from about 1:4 to about 1:1.

The onset of melting point (first detectable melting point) for the overall composition is from about 46° C. to about 90° C.

Generally, for this hair care composition, crystallization point(s) of the composition are usually not less than about 46° C.

The hair composition may be in a form chosen from a liquid, a solution, an emulsion, a cream, a gel, a paste, a mousse, a foam, or any other form that is suitable for application to keratin fibers.

Examples of the hair care composition include but are not limited to the following:

|  | Example #1 | Example #2 | Example #3 | Example #4 | Example #5 | Example #6 | Example #7 | Example #8 | Example #9 | Example #10 |
|---|---|---|---|---|---|---|---|---|---|---|
| Deionized Water | QS | QS | QS | QS | QS | QS | QS | QS | QS | QS |
| Behentrimonium Chloride | 4 |  |  | 3 | 1.71 |  |  |  | 1.5 |  |
| Behenamidopropyl Dimethylamine |  | 4 |  |  |  | 2.14 |  | 3 | 1.5 |  |
| Behentrimonium Methosulfate |  |  | 4 |  |  |  | 2.57 |  |  | 1.67 |
| Behenyl Alcohol |  |  | 1 | 0.5 |  |  | 0.25 | 0.1 |  |  |
| Cetyl Alcohol |  | 2 | 1 | 1 | 1 |  | 0.25 |  |  | 3 |
| Stearyl Alcohol |  | 2 | 2 | 1 | 1 |  |  |  |  | 3 |
| Cetearyl Alcohol | 4 |  |  | 1 |  | 2 | 3 | 3 | 5 |  |
| Arachidyl Alcohol |  |  |  | 0.5 |  |  |  | 0.1 |  |  |
| Paraffin Wax | 3 | 0.25 |  |  |  |  |  | 0.67 |  |  |
| Ozokerite Wax | 0.25 |  |  | 0.25 | 3 | 1 |  |  |  |  |
| Ceresine Wax |  | 3 |  |  |  |  | 0.5 |  |  |  |
| Carnauba Wax |  |  | 0.25 | 3 |  |  |  |  | 0.75 |  |
| Rice Bran Wax |  |  | 3 |  | 0.25 |  |  |  |  | 0.25 |
| pH Adjuster | QS | QS | QS | QS | QS | QS | QS | QS | QS | QS |
| Fragrance | QS | QS | QS | QS | QS | QS | QS | QS | QS | QS |
| Preservative | QS | QS | QS | QS | QS | QS | QS | QS | QS | QS |

What is claimed:

1. A hair care composition consisting of:
   a) 1.5% by weight, behentrimonium chloride;
   b) 1.5% by weight, behenamidopropyl dimethylamine;
   c) 5% by weight, cetearyl alcohol;
   d) 0.75% by weight, carnauba wax; and
   e) deionized water, a pH adjuster, fragrance, and preservative to bring total mass of the composition to 100% by weight.

2. A method for styling hair comprising applying the hair care composition of claim 1 to rinsed hair, massaging through hair for about 5 seconds to about 5 minutes, rinsing composition out of the hair.

3. A method for styling hair comprising applying the composition of claim 1 to damp or towel-dried hair.

\* \* \* \* \*